US006071893A

United States Patent [19]
Graham et al.

[11] Patent Number: 6,071,893
[45] Date of Patent: Jun. 6, 2000

[54] INTERLEUKIN-12 AS AN ADJUVANT FOR PARAMYXOVIRIDAE VACCINES

[75] Inventors: Barney S. Graham; Yi-Wei Tang, both of Nashville, Tenn.

[73] Assignee: Vanderbilt University, Nashville, Tenn.

[21] Appl. No.: 08/980,160

[22] Filed: Nov. 26, 1997

Related U.S. Application Data

[63] Continuation of application No. 08/318,480, Oct. 5, 1994, abandoned.

[51] Int. Cl.$^7$ ..................................................... A61K 48/00
[52] U.S. Cl. .......................... 514/44; 435/320.1; 435/375
[58] Field of Search .......................... 514/44; 435/320.1, 435/69.1, 172.3, 239, 375; 935/62, 57, 55, 56, 34, 65

[56] References Cited

U.S. PATENT DOCUMENTS 5,571,515  11/1996  Scott et al. ............................ 424/208.1

FOREIGN PATENT DOCUMENTS

| 93117244 | 10/1993 | European Pat. Off. . |
| WO94/27636 | 12/1994 | WIPO . |
| WO95/30437 | 11/1995 | WIPO . |

OTHER PUBLICATIONS

Marshall, E. "Gene Therapy's Growing Pains," Science, vol. 269: 1050–1055, Aug. 25, 1995.
Mulligan, R.C. "The Basic Science of Gene Therapy," Science, vol. 260: 926–931, May 14, 1993.
Verma et al. "Gene Therapy–promises, problems, and prospects," Nature, vol. 389: 239–242, Sep. 18, 1997.
Trinchieri, G., "Interleukin–12 and its role in the generation of $T_H1$ cells", Immunology Today, 14(7):335–338 (1993).
Orange, J.S., et al., "Effects of IL–12 on the Response and Susceptibility to Experimental Viral Infections", Journal of Immunology 152:1253–1264 (1994).
Scott, P., "IL–12: Initiation Cytokine for Cell–Mediated Immunity", Science 260:496–497 (Apr. 1993).
Graham, B.S., et al., "Priming Immunization Determines T Helper Cytokine mRNA Expression Patterns in Lungs of Mice Challenged with Respiratory Syncytial Virus", J. Immunol. 151(4):2032–2040 (Aug. 15, 1993).
Tripp, C.S., et al., "Interleukin 12 and tumor necrosis factor are costimulators of interferon γ production by natural killer cells in severe combined immunodeficiency mice with listeriosis, and interleukin 10 is a physiologic antagonist", Proc. Natl. Acad. Sci USA 90:3725–3729 (Apr. 1993).
Heinzel, F.P., et al., "Recombinant Interleukin 12 Cures Mice Infected with Leishmania major", The J. of Exp. Med. 177:1505–1509 (May 1993).
Sypek, J.P., et al., "Resolution of Cutaneous Leishmaniasis: Interleukin 12 Initiates a Protective T Helper Type 1 Immune Response," J. Exp. Med. 177:1797–1802 (Jun. 1993).
Alfonso, L.C.C., et al., "The Adjuvant Effect of Interleukin–12 in a Vaccine Against Leishmania major", Science 263:235–237 (Jan. 14, 1994).

Gazzinelli, R.T., et al., "Interleukin 12 is required for the T–lymphocyte–independent induction of interferon γ by an intracellular parasite and induces resistance in T–cell–deficient hosts", Proc. Natl. Acad. Sci. USA 90:6115–6119 (Jul. 1993).
Gately, M.K., et al., "Regulation of Human Cytolytic Lymphocyte Responses by Interleukin–12", Cellular Immunology 143:127–142 (1992).
Naume, B., et al., "A Comparative Study of IL–12 (Cytotoxic Lymphocyte Maturation Factor)–, IL–2–, And IL–7–Induced Effects On Immunomagnetically Purified CD56$^+$NK Cells", J. Immunology 148(8):2429–2436 (Apr. 15, 1992).
Schoenhaut, D.S., et al., "Cloning and Expression of Murine IL–12", J. of Immunology 148(11):3433–3440 (Jun. 1, 1992).
Morris, S.C., et al., "Effects of IL–12 on in Vivo Cytokine Gene Expression and Ig Isotype Selection", J. of Immunology 152:1047–1056 (1994).
Audibert, F.M., and Lise, L.D., "Adjuvants: current status, clinical perspectives and future prospects", Immunology Today 14(6):281–284 (1993).
Locksley, R.M., "Interleukin 12 in host defense against microbial pathogens", Proc. Natl. Acad. Sci. USA 90:5879–5880 (Jul. 1993).
Hsieh, C–S, et al., "Development of $T_H1$ CD4$^+$T Cells Through IL–12 Produced by Listeria–Induced Macrophages", Science 260:547–549 (Apr. 23, 1993).
Manetti, R., "Natural Killer Cell Stimulatory Factor (Interleukin 12 [IL–12]) Induces T Helper Type 1 (Th1)–specific Immune Responses and Inhibits the Development of IL–4–producing Th Cells", J. Exp. Med. 177:1199–1204 (Apr. 1993).
Chan, S.H., et al., "Induction of Interferon γ Production by Natural Killer Cell Stimulatory Factor: Characterization of the Responder Cells and Synergy with Other Inducers", J. Exp. Med. 173:869–879 (Apr. 1991).
D'Andrea, A., et al., "Production of Natural Killer Cell Stimulatory Factor (Interleukin 12) by Peripheral Blood Mononuclear Cells", J. Exp. Med. 176:1387–1398 (1992).

(List continued on next page.)

Primary Examiner—Karen M. Hauda
Attorney, Agent, or Firm—Hamilton, Brook, Smith & Reynolds, P.C.

[57] ABSTRACT

A method is disclosed of reducing viral replication of a virus of the paramyxoviridae family in a host, comprising administering to the host an antigen of the virus in combination with an effective adjuvant amount of interleukin-12 (IL-12). Human viruses of the paramyxoviridae family include paramyxoviruses (e.g., parainfluenza virus 1, parainfluenza virus 2, parainfluenza virus 3 and parainfluenza virus 4), morbilliviruses (e.g., measles virus) and pneumoviruses (e.g., respiratory syncytial virus); other non-human viruses of the paramyxoviridae family include canine distemper virus, bovine respiratory syncytial virus, Newcastle disease virus and rhinderpest virus. A composition is also disclosed comprising a mixture of an antigen of a virus of the Paramyxoviridae family and an effective adjuvant amount of interleukin-12 (IL-12).

2 Claims, 1 Drawing Sheet

OTHER PUBLICATIONS

Stern, A.S., et al., "Purification to homogeneity and partial characterization of cytotoxic lymphocyte maturation factor from human B–lymphoblastoid cells", *Proc. Natl. Acad. Sci. USA* 87:6808–6812 (Sep. 1990).

Kobayashi, M, et al., "Identification And Purification Of Natural Killer Cell Stimulatory Factor (NKSF), A Cytokine With Multiple Biologic Effects On Human Lymphocytes", *J. Exp. Med.* 170:827–845 (Sep. 1989).

Rabinovich, N.R et al., "Vaccine Technologies: View to the Future", *Science*, 265(5177):1401–1404 (Sep. 2, 1994).

Tang, Y.–W. and Graham, B.S., "Interleukin–12 Treatment during Immunization Elicits a T Helper Cell Type 1–like Immune Response in Mice Challenged with Respiratory Syncytial Virus and Improves Vaccine Immunogenicity", *J. of Infectious Diseases*, 172(3):734–738 (1995).

Li, X., "Protection against Respiratory Syncytial Virus Infection by DNA Immunization", *J. Exp. Med.*, 188(4):681–688 (1998).

INTERLEUKIN-12 AS AN ADJUVANT FOR PARAMYXOVIRIDAE VACCINES

RELATED APPLICATION

This application is a continuation of application Ser. No. 08/318,480 filed Oct. 5, 1994, now abandoned, which is incorporated herein by reference in its entirety.

GOVERNMENT FUNDING

This work was supported in part by the National Institutes of Health Grant RO1-AI-33933. Therefore, the U.S. Government has certain rights in the invention.

BACKGROUND

Respiratory syncytial virus (RSV), a member of the Pneumovirus genus of the Paramyxoviridae family, is an important cause of respiratory disease in infants and children (Connors, M., et al., *J. of Virol.,* 66:7444–7451 (1992). The immunological basis for the differing susceptibility among individuals, and for the limited age range at which severe illness occurs, remains unclear.

The major impediment to advancing new candidate vaccines directed against RSV to clinical trials is an incomplete understanding of the vaccine-enhanced illness caused by formalin-inactivated RSV vaccines in the 1960's. Clinical trials of a formalin-activated alum-precipitated RSV vaccine in the 1960's showed that the vaccine elicited complement-binding antibodies but failed to protect against infection in children. In addition, the illness after subsequent infection was unusually severe with some deaths, and an increased rate of hospitalization (Kapikian, A. Z., et al. *Amer. J. Epidem.,* 89:405 (1969); Fulginti, V. A., et al, *Amer. J. Epidem.,* 89:435 (1969); Kim, W. H., *Amer. J. Epidemol.,* 89:422 (1969); Chin, J. R., et al. *Amer. J. Epidem.,* 89:449 (1969)). A similar enhanced illness can be induced in mice previously immunized with the formalin-inactivated vaccine upon RSV infection, but not in mice immunized with live RSV (Conners, M., et al., *J. Vilrol.* 66:7441 (1992); Graham, B. S., et al., *Immunol.* 151:2032 (1993); Alwan, W. H., et al., *J. Exp. Med.* 179:81 (1994)). Clinical trials of live attenuated RSV vaccine products have not been associated with enhanced illness. Although the live RSV vaccines did not result in enhanced pulmonary disease upon natural infection, the vaccines were, in other respects, as equally unsuccessful as the formalin-inactivated alum-precipitated RSV vaccines (Kim, W. H., et al., *Pediatrics,* 48:745 (1971); Kim, W. H., et al., *Pediatrics,* 52:56 (1973); Belshe, R. B., et al., *J. Infect. Dis.,* 145:311 (1982); Wright, R. B., et al., *Infect. Immun.,* 37:397 (1982). Temperature-sensitive mutants of RSV, cold-adapted RSV or live RSV given parenterally have been considered unsuccessful as vaccines because of high rates of reversion to wild-type, unacceptable virulence or lack of immunogenicity in the appropriate age group (Graham, B. S., et al., *J. of Immun.,* 151:2032–2040 (1993).

Thus, a need exists for development of efficacious methods of vaccination against RSV and for vaccine compositions.

SUMMARY OF THE INVENTION

The present invention is based on the discovery that IL-12 has a potent adjuvant effect for immunizing against Paramyxoviridae virus infection. In one embodiment, the invention comprises a method of reducing viral replication of a virus of the paramyxoviridae family in a host (e.g., mammalian, including human, and avian) comprising administering to the host an antigen of the virus in combination with an effective adjuvant amount of interleukin-12 (IL-12). Human viruses of the Paramyxoviridae family include paramyxoviruses (e.g., parainfluenza virus 1, parainfluenza virus 2, parainfluenza virus 3, parainfluenza virus 4 and mumps virus), morbilliviruses (e.g., measles virus) and pneumoviruses (e.g., respiratory syncytial virus); other non-human viruses of the Paramyxoviridae family include canine distemper virus, bovine RSV, Newcastle disease virus and rhinderpest virus. In one embodiment, the invention relates to a method of reducing replication of the respiratory syncytial virus (RSV) in a host comprising administering to the host an antigen of RSV in combination with an effective adjuvant amount of IL-12. Thus, the present invention also relates to a method of eliciting an immune response against viruses of the Paramyxoviridae family in a host, comprising administering to the host an antigen of a virus of the Paramyxoviridae family in combination with an effective adjuvant amount of IL-12. The present invention also relates to a method of immunizing a host against RSV comprising administering to the host a mixture comprising an antigen of respiratory syncytial virus in combination with an effective adjuvant amount of interleukin-12.

In addition, the present invention relates to a composition comprising a mixture of an antigen of a virus of the Paramyxoviridae family and an effective adjutant amount of interleukin-12 (IL-12). In one embodiment, the invention relates to a composition comprising an antigen of the respiratory syncytial virus and IL-12.

As shown herein, exogenous IL-12 treatment administered at the time of immunization with RSV antigen, diminishes RSV replication and increases endogenous IL-12 mRNA expression at the time of subsequent RSV challenge. This results in a shift from a Th2 to a Th1-like pattern of cytokine expression and a consequent shift in antibody isotype utilization. These results demonstrate that IL-12 is a potent adjuvant for Paramyxoviridae vaccines.

DETAILED DESCRIPTION OF THE INVENTION

Figure 1:
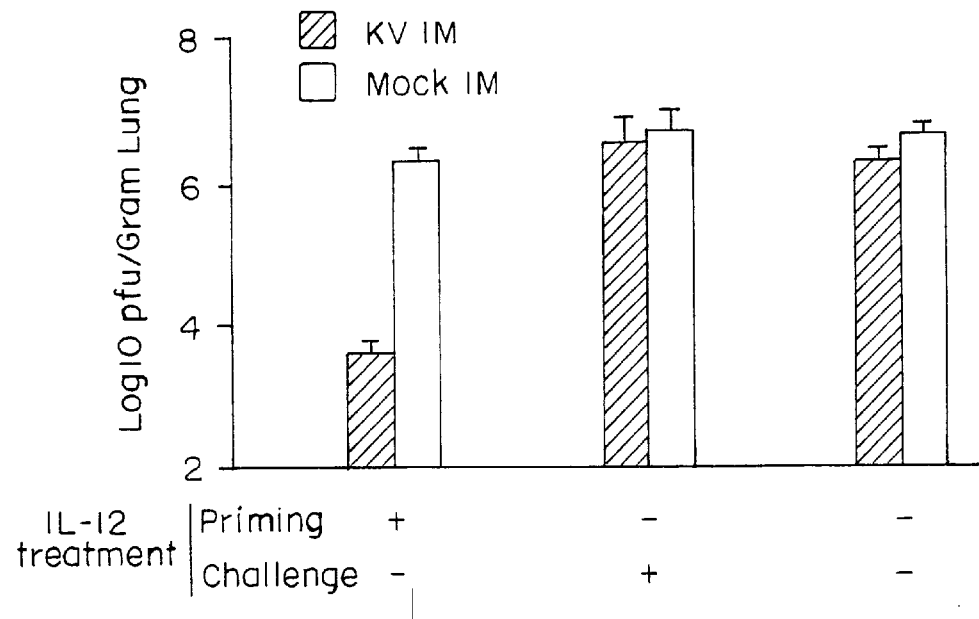
FIG. 1 is a bar graph of IL-12 treatment versus log 10 plaque forming units (pfu)/ gram lung from the plaque assay illustrating that IL-12 administered at the time of immunization has a marked effect on the reduction of viral replication.

The present invention relates to a method of reducing viral replication of a virus of the Paramyxoviridae family in a host (e.g., mammal, including human, avian) comprising, administering to the host, a mixture of an antigen of the virus and an effective adjuvant amount of interleukin-12 (IL-12). Although the method of the present invention is exemplified using RSV, the method can be used to reduce viral replication of a variety of viruses from the Paramyxoviridae family which include human paramyxoviridae viruses, such as paramyxoviruses (e.g., parainfluenza virus 1, parainfluenza virus 2, parainfluenza virus 3, parainfluenza virus 4 and mumps virus), morbilliviruses (e.g., measles virus) and pneumoviruses (e.g., respiratory syncytial virus). Other non-human viruses of the Paramyxoviridae family include canines distemper virus, bovine RSV, Newcastle disease virus and rhinderpest virus. In one embodiment, the method of the present invention is used to reduce viral replication of respiratory syncytial virus (RSV) in a host, and comprises administering to the host an RSV antigen and an effective adjuvant amount of IL-12.

In another embodiment, the method of the present invention is used to elicit an immune response against a virus of the Paramyxoviridae family in a host, comprising administering to the host an antigen of the virus and an effective adjuvant amount of IL-12. In addition, the present invention relates to a method of immunizing a host against RSV comprising administering to the host a mixture comprising an RSV antigen and an effective adjuvant amount of IL-12.

An antigen of a virus of the Paramyxoviridae family includes use of the whole virus (e.g., inactivated or live, attenuated whole virus), an antigenic portion of the virus, and recombinantly produced virus or portions thereof or fusion proteins. In addition, antigens of the present invention include nucleic acid sequences which encode an antigen of a virus of the Paramyxoviridae family. Antigenic portions of the viruses of the Paramyxoviridae family include the fusion glycoprotein (F protein) and the hemagglutinin-neuraminidase of the parainfluenza viruses 1, 2, 3, 4; the F protein and the hemagglutinin-neuraminidase of the mumps virus; the F protein and the hemagglutinin-neuraminidase of the measles virus; and the F protein and the G glycoprotein of the RSV. Other antigenic portions of the Paramyxoviridae family of viruses which can be used in the methods and compositions of the present invention, can be determined by those of ordinary skill in the art.

The IL-12 of the present invention can be obtained from a suitable source for use in the present method. For example, IL-12 can be purified from natural sources (e.g., human, animal), produced by chemical synthesis or produced by recombinant DNA techniques as described in Example 1. In addition, the IL-12 of the present invention include nucleic acid sequences encoding IL-12, as well as the RNAs encoded by such nucleic acid sequences. As used herein, "interleukin-12" and "IL-12" refer to interleukin 12, its individual subunits, fragments thereof which exhibit IL-12 adjuvant activity and functional equivalents of "interleukin-12" and "IL-2". Functional equivalents of "interleukin-12" and "IL-12" include modified IL-12 protein such that the resulting IL-12 product has the same adjuvant activity as the IL-12 described herein, and nucleic acid sequences which through the degeneracy of the genetic code encode the same peptide gene product as IL-12 and having the IL-12 adjuvant activity described herein. For example, a functional equivalent of "interleukin-12" and "IL-12" can contain a "silent" codon or amino acid substitution (e.g., substitution of one acidic amino acid for another acidic amino acid; or substitution of one codon encoding a hydrophobic amino acid to another codon encoding a hydrophobic amino acid).

IL-12, a heterodimeric cytokine predominantly excreted by the macrophage cells, has been reported to enhance NK cell and CTL activity, to stimulate the differentiation of Th1 cells, and to induce production of cytokines, such as IFN-γ (Gately, M. K., et al, *Cell. Immunol.* 143:127 (1992); Naume, B., et al, *J. Immunol.* 148:2429 (1992); Hsieh, C. S., et al *Science* 260:547 (1993); Manetti, R., et al *J. Exp. Med.* 177:1199 (1993); Chan, S. H., et al, *J. Exp. Med.* 173:869 (1991); D'Andrea, A., et al, *J. Exp. Med.* 1,76:1387 (1992); Macatonia, S. E., et al, *Int. Immunol.* 5:1119 (1993); Tripp, C. S., et al, *Proc. Natl. Acad. Sci. USA* 90:3725 (1993)). IL-12 formerly referred to as natural killer cell stimulatory factor or cytotoxic lymphocyte maturation factor functions to activate and to link the innate and acquired immune responses (Kobayashi, M., et al *J. Exp. Med.* 170:827 (1989); Stern, A. S., et al *Proc. Natl. Acad. Sci. USA* 87:6808 (1990); Locksley, R. M., et al *Proc. Natl. Acad. Sci. USA* 90:5879 (1993)). IL-12 promotes differentiation of uncommitted T helper cells towards the Type 1 (Th1) phenotype (Hsieh, C. S., et al *Science* ?60:547 (1993); Manetti, R., et al *J. Exp. Med.* 177:1199 (1993)). This results in a characteristic constellation of cytokines, such as IFN-γ, and generally promotes cell-mediated immunity (Chan, S. H., et al, *J. Exp. Med.* 173:869 (1991); D'Andrea, A., et al, *J. Exp. Med.* 176:1387 (1992) Macatonia, S. E., et al, *Int. Immunol.* 5:1119 (1993); Gately, M. K. , et al, *Cell. Immunol.* 143:127 (1992) Naume, B., et al, *J. Immunol.* 148:2429 (1992)). IL-12 has been demonstrated to enhance the immune response and to improve protective immunity in several infectious disease models, including Listeriosis, Leishmaniasis, Toxoplasmosis and lymphocytic choriomeningitis virus infection (Tripp, C. S., et al, *Proc. Natl. Acad. Sci. USA* 90:3725 (1993); Heinzel, F. P., et al *J. Exp. Med.* 77:1505 (1993); Sypek, J. P., et al *J. Exp. Med.* 177:1797 (1993); Afonso, L. C., et al, *Science* 263:235 (1994); Gazzinelli, R. T., et al, *Proc. Natl. Acad. Sci. USA* 90:6115 (1993); Khan, I. A., et al *Infect. Immun.* 62:1639 (1994); Orange, J. S. et al, *J. Immunol.* 152:1253 (1994)). The purification and cloning of IL-12 are disclosed in PCT publication nos. WO 92/05256 and WO 90/05147, and in European patent publication no. 322,827 (identified as "CLMF").

Interleukin-12 or IL-12 is a mammalian cytokine which exhibits numerous immunologic effects, including modulation of T cell response to antigens (see, for example, PCT publication nos. WO 92/05256 and WO 90/05147, where:n IL-12 is identified as "NKSF"). It has also been suggested generally that IL-12 might have some application as a vaccine adjuvant (Scott, P., Science, 260:496–497(1993); Trichieri, G., Immunology Today, 14:335–338(1993)).

In the method of the present invention, an effective adjuvant amount of IL-12 is administered in combination with an antigen of a virus of the Paramyxoviridae family. That is, the IL-12 is administered at a time closely related to immunization of the host with the viral antigen, so that an enhanced immune response in the host is produced relative to the immunization of a host in which IL-12 is not administered. Thus, the IL-12 can be administered prior to, preferably just prior to, immunization, at the time of immunization (i.e., simultaneously) or after immunization (i.e. subsequently). In addition, the IL-12 can be administered prior to immunization with the viral antigen of the Paramyxoviridae family, followed by subsequent injections of IL-12 after immunization with the antigen.

The IL-12 and the antigen can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the IL-12 and the antigen of the Paramyxoviridae virus can be administered together with other components or biologically active agents, such as other known adjuvants (e.g., alum, MPL, QS21), pharmaceutically acceptable surfactants (e.g., glycerides), excipients (e.g., lactose), carriers, diluents and vehicles. If desired, certain sweetening, flavoring and/or coloring agents can also be added.

The IL-12 and the antigen can be administered as a prophylactic vaccine to hosts which are either infected or uninfected with the virus. The IL-12 and the antigen can also be administered as a therapeutic vaccine to infected hosts and can result in amelioration or elimination of the disease state caused by the infecting virus.

Further, the antigen and/or IL-12 can be administered by in vivo expression of polynucleotides encoding such into a mammalian subject. For example, the IL-12 or the Paramyxoviridae antigen can be administered to a host using live vectors, wherein the live vectors containing IL-12 and/or antigen nucleic acid sequences are administered under conditions in which the antigen and/or IL-12 are expressed in vivo. For example, a host can be injected with a vector which encodes and expresses an antigen of a virus of the Paramyxoviridae family in vivo in combination with IL-12 protein or peptide, or in combination with a vector which encodes and expresses the IL-12 protein in vivo. Alternatively, a host can be injected with a vector which encodes and expresses IL-12 in vivo in combination with a Paramyxoviridae antigen in peptide or protein form, or in combination with a vector which encodes and expresses a Paramyxoviridae antigen in vivo. A single vector containing the sequences encoding a Paramyxoviridae antigen and the IL-12 protein are also useful in the methods and compositions of the present invention.

Several expression vector systems are available commercially or can be reproduced according to recombinant DNA and cell culture techniques. For example, vector systems such as the yeast or vaccinia virus expression systems, or virus vectors can be used in the methods and compositions of the present invention (Kaufman, R. J., *A J. of Meth. in Cell and Molec. Biol.*, 2:221–236 (1990)). Other techniques using naked plasmids or DNA, and cloned genes encapsidated in targeted liposomes or in erythrocytes ghosts, can be used to introduce the IL-12 and/or Paramyxoviridae antigen polynucleotides into the host (Freidman, T., *Science*, 244:1275–1281 (199); Rabinovich, N. R., et al., *Science*, 265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molecular Cloning, Cold Spring Harbor Press*, 1989; Ausubel, F. M., et al., *Current Protocols in Molecular Biology*, Greene Publishing Associates and Wiley-Interscience, 1989).

The amount of antigen used in the methods and compositions of the present invention is an amount which produces an effective immunostimulatory response in the host. An effective adjuvant amount of IL-12 is an amount such that when administered, it results in an enhanced immune response relative to the immune response when an effective adjuvant amount of IL-12 is not administered. In addition, the amount of antigen from a virus of the Paramyxoviridae family and IL-12 used to immunize the host will vary depending on a variety of factors, including the antigen employed, the size, age, body weight, general health, sex and diet of the host, and the time of administration, duration or particular qualities of the Paramyxoviridae virus being vaccinated against. Adjustment and manipulation of established dosage ranges are well within the ability of those skilled in the art.

The formulation and route of delivery of vaccine products can influence the induction of T helper lymphocyte subsets and may thereby affect disease expression after viral challenge (Graham, B. S., et al, *Immunol.* 151:2032 (1993)). Depletion of IL-4 at the time of immunization by neutralizing monoclonal antibody induces a Th2 to Th1-like immune response shift, accompanied by an improved clinical outcome and an increased CD8+ cytotoxic T lymphocyte (CTL) activity (Tang, Y.-W., et al, *J. Clin. Invest.* (1994)). This was associated with an increased expression of endogenous IL-12 message at the time of challenge in the anti-IL-4 treated mice. These findings suggest that selective activation of the Th2-like cell subset may be responsible for RSV vaccine induced immunopotentiation of disease and that IL-12 may be associated with shifting the response away from Th2 to a more Th1-like response.

Replication of RSV is markedly reduced after live RSV challenge in mice given IL-12. Use of IL-12 as an adjuvant in a composition comprised of an antigen from RSV and IL-12 also induced a shift from a Th2 to a Th1-like immune response in mice after RSV challenge. While the IL-12 adjuvant effect was potent for reduction of RSV replication, it is more important for use as a vaccine adjuvant to decrease illness following challenge by RSV. The use of cytokines as adjuvants can allow one to control the immune parameters induced by immunization to improve protective effects and decrease the negative effects of a vaccine for RSV. The effects of IL-12 on the immune responses to RSV vaccination as measured after live virus challenge in the BALB/c mouse model are described in the Examples. The results indicate that IL-12 acts as a potent adjuvant and is a useful product to include in RSV vaccines.

As described in Example 1, BALB/c mice were immunized with inactivated whole virus intramuscularly, and murine recombinant IL-12 was administered intraperitoneally for 5 successive days starting at one day before immunization or challenge. The mice were challenged with live virus 4 weeks later. The viral replication in lungs 4 days after challenge was assessed. IL-12 administered at the time of immunization had a marked effect on the reduction of viral replication. Log 10 pfu per lung was reduced from 6.9 in RSV-immunized control mice without IL-12 administration to 3.8 in immunized mice with IL-12 administration (FIG. 1). In contrast, IL-12 administration at the time of challenge did not have significant effect on the viral replication (FIG. 1).

The effects of different delivery routes for IL-12 is described in Example 2. IL-12 was administered either intraperitoneally as described in Example 1, or intramuscularly mixed with the RSV immunogen. Table 1 shows the effect of either intraperitoneal or intramuscular delivery of IL-12 on the reduction of viral replication. A single dosage of IL-12 given simultaneously with immunogen had the same effect on the reduction of viral replication compared to the 5-dosage intraperitoneal regimen. IL-12 as a specific immunomodulator only worked in RSV immunized mice, having no effects on the unprimed mice (FIG. 1, Table 1). These data demonstrate that IL-12 exerts a potent adjuvant effect on the inactivated RSV immunogen.

The patterns of immunoglobulin isotypes produced in response to immunization are indirect indicators of the types of cytokines produced in vivo. IgG2a is produced in mice as a consequence of Th1cell activation, whereas IL-4 promotes the production of IgG1 (Burstein, H. J. et al, *J. Immunol.* 147:2950 (1991); Finkelman, F. D., et al, *Annu Rev. Immunol.* 8:303 (1990); Morris, S. C., et al, *J. Inmuunol.* 152:1047 (1994)). As described in Example 3, blinded assays of serum RSV-specific immunoglobulin isotype titers in RSV-immunized mice receiving IL-12 showed that IL-12 induced significantly more RSV-specific IgG2a antibody and significantly less IgG1 antibody compared to immunized mice not given IL-12. The pattern of IgG2a and IgG1 RSV-specific antibody response was similar whether IL-12 was given intramuscularly or intraperitoneally (Table 2).

Figure 2:
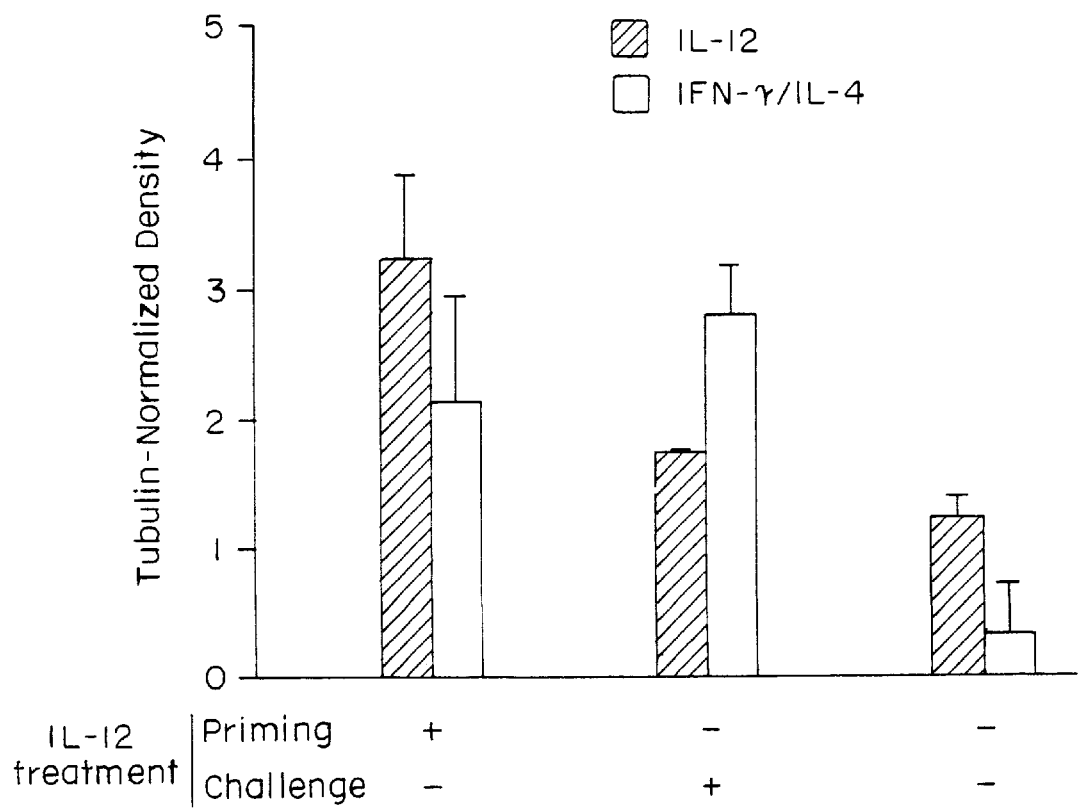
FIG. 2 is a bar graph of IL-12 treatment versus averaged α-tubulin-normalized density from the mRNA Northern blots illustrating that IL-12 enhanced Th1 cell differentiation and produced a shift from a Th2 to a Th1-like response in mice immunized with inactivated RSV immunogen.

The pattern of antibody isotype utilization induced by IL-12 suggests that in vivo IL-12 administration can promote the differentiation of antigen-specific CD4+ Th1 cells and inhibit the development of Th2 cells in response to the inactivated RSV intramuscular immunization. The pattern of cytokine mRNA expression in lungs was directly examined as described in Example 4. Lung tissues from immunized mice, with or without IL-12 treatment, were harvested at 4 days after live virus challenge. The cytokine mRNAs for IFN-γ, IL-4, IL-6, IL-10, and IL-12, were measured by Northern blot analysis. There were no obvious differences in IL-6 and IL-10 mRNA levels among mice with different treatments. However, the lungs from mice treated with IL-12 at the time of either immunization or challenge contained more IFN-γ relative to IL-4 compared to control mice that did not receive IL-12 (FIG. 2). Increased IL-12 mRNA expression occurred in the mice treated with IL-12 at the time of immunization, while IL-12 administration at challenge did not increase IL-12 mRNA expression (FIG. 2). These data suggest that IL-12 enhanced Th1 cell differentiation and produced a shift from a Th2 to a Th1-like response in mice immunized with the inactivated RSV immunogen.

RSV-specific cytotoxic T lymphocyte (CTL) activity in lungs of immunized mice was assessed to evaluate whether IL-12 administration enhanced cell-mediated immunity as a positive modulatory effector. As described in Example 5, a direct CTL assay using lung lymphocytes was employed which does not include in vitro stimulation (Tang, Y.-W., et al, *J. Clin. Invest.* (1994)). There was no difference in CTL activity between groups that received or did not receive IL-12 treatment at the time of immunization. This result, which was repeated in two consecutive experiments, further suggests the Th1-like cytokine pattern was a product of CD4+ T cells. It is reasonable to expect that altering the dose of IL-12 would induce a greater CD8+ response which would alter the illness pattern.

As described in Example 5, even though IL-12 has a dramatic effect on the reduction of RSV replication in lungs, there was not significant difference in the clinical outcome, including weight loss and illness score between groups. The simple shift in the pattern of cytokine expression was therefore not predictive of a change in illness. This suggests that the cell populations responsible for cytokine production can be key determinants of illness and not cytokines themselves. For example, mice treated with anti-IL-4 at the time of immunization also had increased IFN-γ expression in lungs at the time of challenge. However, the anti-IL-4 treatment resulted in diminished illness that was associated with increased CD8+CTL activity (Tang, Y.-W., et al, *J. Clin. Invest.* (1994)). In the case of anti-IL-4 treated mice, it may be that the IFN-γ was a product of CD8+ T cells, whereas in IL-12 treated mice, CD4+ T cells are a more likely source.

Adjusting the dose of IL-12 can alter its properties. A recent study of IL-12 on immune responses to lymphocytic choriomeningitis (LCMV) infection showed that low doses of IL-12 enhanced immunity to LCMV infection as demonstrated by increased splenic CD8+ T cell numbers and decreased LCMV replication. However, high doses of IL-12, equivalent to those used in the examples, impaired resistance against LCMV infection as demonstrated by reduced virus-specific CTL activity and increased viral replication (Orange, J. S. et al, *J. Immunol.* 152:1253 (1994)). It may therefore be possible to adjust the dose of IL-12 or its method cf delivery to maintain the effect on viral inhibition, but to also impact illness.

The invention is further illustrated in the following examples.

EXEMPLIFICATION

EXAMPLE 1

Immunization of Mice With RSV and IL-12 Mice

Pathogen-free female BALB/c mice, 8 to 10 months old, were purchased from Charles River Laboratories (Raleigh, N.C.) and cared for according to the "Guide for the Care and Use of Laboratory Animals" as previously described (Graham, B. S., et al, *J. Med. Virol.* 26:153 (1988)).

RSV Immunogen and Virus

Preparation of the formalin-inactivated alum-precipitated RSV and preparation of stock of the A2 strain of RSV have been previously reported (Graham, B. S., et al, *Immunol.* 151:2032 (1993)). Both the vaccine preparation and the challenge stock were derived from the A2 strain of RSV.

Murine Cytokine IL-12

Murine recombinant IL-19 was expressed from cloned cDNAs (Schoenhaut, D. S., et al, *J. Immunol.* 148:3433 (1992)). The lot used in this paper was MRB021693-1.2 (Genetics Institute, Cambridge, Mass.) with a specific activity of $5.6 \times 10^6$ units/mg as determined by PHA blast assay (Wolf, S. F., et al, *J. Exp. Med.* 146:3074 (1991)). Concentrated aliquots of IL-12 were stored at $-70°$ C. and diluted in phosphate-buffered saline with 1% normal mouse serum (1% PBS).

Immunization

Mice were immunized with formalin-inactivated alum-precipitated RSV containing $2.2 \times 10^6$ pfu equivalents of virus antigen intramuscularly, and challenged with $10^7$ pfu of live RSV intranasally 4 weeks later as previously described (Graham, B. S., et al, *Immunol.* 151:2032 (1993)); Tang, Y.-W., et al, *J. Clil. Invest.* (1994)). IL-12 was administered intraperitoneally for 5 successive days, starting at one day before immunization at a dose of 1 μg/mouse. Control mice received 1% phosphate buffered saline (PBS) on the same schedule.

The viral replication in lungs 4 days after challenge was assessed by plaque assay. Mouse serum samples were collected on the day of and two weeks after live RSV challenge.

Plaque Assays and Neutralization Tests

Two-day old HEp-2 monolayers, 80% confluent in Costar 12-well plates, were used for plaque assay and neutralization tests. The assays were performed as described previously (Graham, B. S., et al, *J. Med. Virol.* 26:153 (1988)).

IL-12 administered at the time of immunization has a marked effect on the reduction of viral replication. Log 10 pfu per lung was reduced from 6.9 in RSV-immunized control mice without IL-12 administration to 3.8 in immunized mice with IL-12 administration. In contrast, IL-12 administration at the time of challenge did not have significant effect on the viral replication. See FIG. 1. (Log 10 pfu/gram lung is shown as arithmetic means±S.D.; KV denotes killed virus)

EXAMPLE 2

Effect of Delivery Route of IL-12 on its Adjuvant Ability

The effect of a different delivery route of the adjuvant IL-12 was assessed. IL-12 was administered intraperitoneally as described in Example 1 to one group of mice. To another group of mice, IL-12 was administered intramuscularly mixed with the RSV antigen. The control mice were either mock immunized or treated with IL-1:2 alone without antigen. Table 1 summarizes the results of the experiment which show that a single dosage of IL-12 given simultaneously with immunogen had the same effect on the reduction of viral replication compared to the 5-dosage intraperitoneal regimen. IL-12 as a specific immunomodulator only worked in RSV immunized mice, having no effects on the unprimed mice. See FIG. 1 and Table 1. These data demonstrate that IL-12 exerted a potent adjuvant effect on the inactivated RSV immunogen.

EXAMPLE 3
Assay of Immunoglobulin Isotype Titers in RSV-immunized Mice Receiving IL-12

The patterns of immunoglobulin isotypes produced in RSV-immunized mice receiving IL-12 was examined. Mouse serum samples were collected on the day of and two weeks after live RSV challenge.
RSV-Specific Immunoglobulin Isotype ELISA All serologic assays were performed by a person blinded to the experimental groups. BCH4 and BC cells were bound to the solid phase on Immulon II 96-well plates (NUNC, Denmark). Serial diluted mouse serum samples were added to each well. Plates were incubated, washed, and goat anti-murine IgG1 or IgG2a conjugated to alkaline phosphatase (Southern Biotechnology, Birmingham, Ala.) diluted 1:1000 was added, respectively. After another incubation, plates were washed and substrate was added for 30 minutes at room temperature and $OD_{405}$ was determined (Graham, B. S., et al, Immunol. 151:2032 (1993); Tang, Y.-W., et al, J. Clin. Invest. (1994)). A serum dilution was considered positive if the mean optical density of two BCH4 cell wells was greater than twice that of BC-coated wells and greater than 0.1.

The results demonstrate that IL-12 induced significantly more RSV-specific IgG2a antibody and significantly less IgG1 antibody compared to immunized mice not given IL-12. The pattern of IgG2a and IgG1 RSV-specific antibody response was similar whether IL-12 was given intramuscularly or intraperitoneally. See Table 2.

EXAMPLE 4
Pattern of Cytokine mRNA Expression in Lungs From Mice Immunized With and Without IL-12

Lung tissues from immunized mice, with and without IL-12 treatment, were harvested at 4 days after live virus challenge. The cytokine mRNAs for IFN-γ, IL-4, IL-6, IL-10 and IL-12 were measured by Northern blot analysis.
mRNA Extraction, Northern Blotting, and Cytokine Detection The total RNA from whole lungs was extracted and polyA RNA isolated, electrophoretically separated and transferred to membrane as previously described (Graham, B. S., et al, Immunol. 151:2032 (1993); Tang, Y.-W., et al, J. Clin. Invest. (1994)). Hybridization with $^{32}P$ oligonucleotide probes were performed as previously described (Graham, B. S., et al, Immunol. 151:2032 (1993)). After washing, membranes were exposed to Kodak X-omat film at −70° C. Laser densitometry was performed with an LKB UltroScan XL using GelScan XL software (Pharmacia Fine Chemicals, Piscataway, N.J.). Oligonucleotide probes for murine IL-4, IL-10, IFN-γ, IL-6 were purchased from R & D Systems (Minneapolis, Minn.) or Clontech Laboratory Inc. (Palo Alto, Calif.). A cocktail of oligonucleotides designed for detecting IL-12 was based on the murine IL-12 sequence spanning predicted splice sites based on those identified in the human IL-12 sequence. (Schoenhaut, D. S., et al, J. Immunol. 148:3433 (1992)). From 5' to 3':
p-40:

TGAGGACACATCTTGCTTTGCTGCGAGCTG(SEQ. ID. NO:1),

TCCCGCCTTTGCATTGGACTTCGGTGATG (SEQ. ID. NO:2), and

CAACGTTGCATCCTAGGATCGGACCCTGCA(SEQ. ID. NO:3);

p-35:

GCCAGGCAACTCTCGTTCTTGTGTAGTTCC (SEQ. ID. NO:4), and

GCGTTGATGGCCTGGAACTCTGTCTGGTAC(SEQ. ID. NO:5).

Cytokine mRNA Northern blots (2 samples per group) with averaged α-tubulin-normalized densities are shown in FIG. 2. There were no obvious differences in IL-6 and IL-10 mRNA levels among mice with different treatments. However, the lungs from mice treated with IL-12 at the time of either immunization or challenge contained more IFN-γ relative to IL-4 compared to control mice that did not receive IL-12 (FIG. 2). An increased IL-12 mRNA expression occurred in the mice treated with IL-12 al the time of immunization, while IL-12 administration at challenge did not increase IL-12 mRNA expression (FIG. 2). These data suggested that IL-12 enhanced Th1 cell differentiation and produced a shift from a Th2 to a Th1-like response in mice immunized with the inactivated RSV immunogen.

EXAMPLE 5
RSV-specific Cytotoxic T Lymphocyte (CTL) Activity in Lungs of Immunized Mice RSV-specific CTL activity in lungs of immunized mice was assessed to evaluate whether IL-12 administration enhanced cell-mediated immunity as a positive modulatory effector. A direct CTL assay using lung lymphocytes was employed which does not include in vitro stimulation (Tang, Y.-W., et al, J. Clin. Invest. (1994)).
Cytotoxicity T Cell Assays Whole lung lymphocytes were isolated by Ficoll-Hypaque (1.09 specific gravity) cushion centrifugation. BCH4 and BC target cells labeled with $^{51}Cr$ (Dupont-New England Nuclear, Boston, Mass.) were incubated with effector cells for 4 hours at 37° C. in 96-well microtiter plates as described (Tang, Y.-W., e;; al, J. Clin. Invest. (1994)). The spontaneous and total release were obtained by treating the target cells with 10% RPMI and 5% Triton X-100 detergent, respectively. Each point was the mean from three replicate wells. The specific release of $^{51}Cr$ from target cells was defined as 100× (sample cpm—background cpm)/(total cpm—background cpm).

There was no difference in CTL activity between groups that received or did not receive IL-12 treatment at the time of immunization. This result was repeated in two consecutive experiments and further suggests the Th1-like cytokine pattern was a product of CD4+ T cells. Even though IL-12 has a dramatic effect on the reduction of RSV replication in lungs, there was no significant difference in the clinical outcome, including weight loss and illness score between groups. Illness assessment, including weight loss and clinical scores were performed as previously described (Tang, Y.-W., et al, *J. Clin. Invest.* (19941)). The simple shift in the pattern of cytokine expression was therefore not predictive of a change in illness. This suggests that the cell population responsible for cytokine production may be a key determinant of illness and not cytokines themselves. For example, mice treated with anti-IL-4 at the time of immunization also had increased IFN-γ expression in lungs at the time of challenge. However, the anti-IL-4 treatment resulted in diminished illness that was associated with increased CD8+ CTL activity (Tang, Y.-W., et al, *J. Clin. Invest.* (1994) ). In the case of anti-IL-4 treated mice, it may be that the IFN-γ was a product of CD8+ T cells, whereas in IL-12 treated mice, CD4+ T cells were a more likely source.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

TABLE 1

IL-12 Administered Either Intraperitoneally or Intramuscularly Reduces Virus Replication in Lungs and Noses

| Group | N | Immunogen | IL-12 Route | Log 10 pfu/gram Lung* | Log 10 pfu/Nose* |
|---|---|---|---|---|---|
| 1 | 5 | KV | — | 6.56 ± 0.44 | 3.73 ± 0.15 |
| 2 | 5 | KV | IP | 4.75 ± 0.25† | 2.61 ± 0.23‡ |
| 3 | 5 | KV | IM | 4.44 ± 0.55† | 2.80 ± 0.34‡ |
| 4 | 5 | Mock | — | 6.55 ± 0.32 | 3.73 ± 0.29 |
| 5 | 5 | Mock | IP | 6.51 ± 0.34 | 3.21 ± 0.27 |

*Mean ± S.D.
†p <0.001 compared to Log 10 pfu/gram lung in group 1
‡p <0.001 compared to log 10 pfu/nose in group 1
KV killed virus
IP intraperitoneal
IM intramuscularly

TABLE 2

IL-12 Administered Alters RSV-Specific Serum Immunoglobulin Isotype Titers at and Two Weeks After RSV Challenge

| Group | Immunogen | IL-12 Route | At Challenge | | 2 Weeks After Challenge | |
|---|---|---|---|---|---|---|
| | | | IgG1 | IgG2a | IgG1 | IgG2a |
| 1 | KV | — | <80 (0/5)* | <80 (0/5) | 640.0 ± 2.2 (4/4) | 269.1 ± 4.2 (2.4) |
| 2 | KV | IP | <80 (0/5) | 557.2 ± 6.4† (3/5) | 121.3 ± 1.9‡ (2/5) | 640.0 ± 6.7‡‡ (3/5) |
| 3 | KV | IM | <80 (0/5) | 367.6 ± 4.1 (3/5) | <80 (0/5) | 905.1 ± 4.2‡‡ (3.4) |
| 4 | Mock | — | <80 (0/5) | <80 (0/5) | <80 (0/5) | 113.1 ± 2.1 (1/4) |
| 5 | Mock | IP | <80 (0/5) | <80 (0/5) | <80 (0/5) | 139.3 ± 2.5 (2/5) |

*Number converted/number tested
†Geometric mean titer ± S.D. Negative samples were assigned a titer value of 80 for statistical calculations.
‡p < 0.01 compared to IgG1 2 weeks after challenge in group 1
‡‡p > 0.5 compared to IgG2a 2 weeks after challenge in group 1
KV killed virus
IP intraperitoneal
IM intramuscular

We claim:

1. A method of reducing replication of a respiratory syncytial virus in a mammal, comprising administering to the mammal a polynucleotide encoding a fusion glycoprotein of the virus in combination with an effective adjuvant amount of IL-12, wherein the antigen is administered under conditions in which the antigen is expressed in vivo thereby reducing replication of the virus in the host.

2. A method of eliciting an immune response against a respiratory syncytial virus in a mammal comprising administering to the mammal a polynucleotide encoding a fusion glycoprotein of the virus in combination with an effective adjuvant amount of IL-12, wherein the antigen is administered under conditions in which the antigen is expressed in vivo thereby eliciting an immune response against the virus in the host.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

-continued

```
TGAGGACACA TCTTGCTTTG CTGCGAGCTG                                    30

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TCCCGCCTTT GCATTGGACT TCGGTGATG                                     29

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CAACGTTGCA TCCTAGGATC GGACCCTGCA                                    30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCCAGGCAAC TCTCGTTCTT GTGTAGTTCC                                    30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGTTGATGG CCTGGAACTC TGTCTGGTAC                                    30
```